United States Patent [19]

Roeper et al.

[11] Patent Number: 5,264,616

[45] Date of Patent: Nov. 23, 1993

[54] PREPARATION OF OMEGA-FORMYLALKANECARBOXYLIC ESTERS

[75] Inventors: Michael Roeper, Wackhenheim; Peter M. Lorz, Mannheim; Dieter Koeffer, Birkenau, all of Fed. Rep. of Germany

[73] Assignee: BASF Aktiengesellschaft, Ludwigshafen, Fed. Rep. of Germany

[21] Appl. No.: 18,495

[22] Filed: Feb. 17, 1993

[30] Foreign Application Priority Data

Feb. 18, 1992 [DE] Fed. Rep. of Germany ....... 4204808

[51] Int. Cl.$^5$ .................... C07C 45/50; C07C 67/38
[52] U.S. Cl. .................................. 560/175; 568/454; 560/177; 560/179
[58] Field of Search ............ 560/175, 177, 179; 568/454, 451; 502/158

[56] References Cited

U.S. PATENT DOCUMENTS

| | | | |
|---|---|---|---|
| 3,253,018 | 5/1966 | Zachry et al. | 260/483 |
| 4,769,498 | 9/1988 | Billig et al. | 568/454 |
| 4,801,738 | 7/1989 | Schneider et al. | 560/177 |
| 4,910,328 | 3/1990 | Bertleff et al. | 560/177 |

FOREIGN PATENT DOCUMENTS

| | | |
|---|---|---|
| 125567 | 1/1986 | European Pat. Off. |
| 131860 | 5/1987 | European Pat. Off. |
| 295554 | 12/1988 | European Pat. Off. |

*Primary Examiner*—Arthur C. Prescott
*Attorney, Agent, or Firm*—Keil & Weinkauf

[57] ABSTRACT

$\omega$-Formyl-$C_4$–$C_{20}$-alkanecarboxylic esters are prepared by reacting $C_4$–$C_{20}$-alkenecarboxylic esters with carbon monoxide and hydrogen at from 30° to 150° C. and under from 0.01 to 30 bar in the presence of rhodium carbonyl complexes which are modified with polyphosphites.

10 Claims, No Drawings

PREPARATION OF OMEGA-FORMYLALKANECARBOXYLIC ESTERS

The present invention relates to a process for preparing ω-formylalkanecarboxylic esters by hydroformylation of alkenecarboxylic esters.

U.S. Pat. No. 3,253,018 and EP-A 295 554 disclose the preparation of ω-formylalkanecarboxylic esters by hydroformylation of ω-alkenecarboxylic esters in the presence of cobalt carbonyl catalysts. However, considerable quantities of branched esters which are unwanted for further use are also produced.

EP-B 125 567 and EP-B 131 860 also described processes in which 3-pentenoic esters or 4-pentenoic esters are hydroformylated in the presence of carbonyl complexes of rhodium which are modified with tertiary organic phosphines or phosphites to give formylvaleric esters. However, the proportion of straight-chain compounds is still in need of improvement.

U.S. Pat. No. 4,769,498 recommends tertiary polyphosphites as ligands for the rhodium-catalyzed hydroformylation. There is no indication of how the proportion of straight-chain compounds in the hydroformylation of alkenecarboxylic esters can be increased further.

It is an object of the present invention to provide a process for preparing ω-formylalkanecarboxylic esters by hydroformylation of alkenecarboxylic esters in which the proportion of straight-chain compounds is maximized, the reaction takes place under moderately elevated pressure with high conversion, and the catalysts have increased stability.

We have found that this object is achieved by a process for preparing ω-formyl-$C_4$-$C_{20}$-alkanecarboxylic esters by reacting $C_4$-$C_{20}$-alkenecarboxylic esters with carbon monoxide and hydrogen at from 30° to 150° C. in liquid phase in the presence of rhodium carbonyl complexes and in the presence of tertiary organic phosphites, which comprises using at least one tertiary organic polyphosphite which has from 2 to 6 phosphorus atoms in the molecule and in which, in each case, one bond on each phosphorus atoms is linked via an oxygen bridge to a substituted or unsubstituted arylene or bisarylene which is at least divalent, to an alkylene which can contain an oxygen in the chain, or to a radical with two isolated aryl radicals via the aryl radicals, and two bonds on each phosphorus atom are linked via an oxygen bridge to a substituted or unsubstituted divalent arylene or bisarylene, to an alkylene or to a radical with two isolated aryl radicals via the aryl radicals, or two bonds on at least one phosphorus atom are, in each case, separately linked via an oxygen ridge in each case to a monovalent substituted or unsubstituted aryl, bisaryl, alkyl, aralkyl or cycloalkyl.

The novel process has the advantage that it results in straight-chain compounds with greater selectivity, while a high conversion is obtained under moderately elevated pressure, and the rhodium catalysts have increased stability.

Starting compounds used according to the invention are $C_4$-$C_{20}$-alkenecarboxylic, especially their $C_1$-$C_4$-alkyl esters. The olefinic double bond can be terminal or internal. $C_1$-$C_4$-alkyl ω-$C_4$-$C_7$-alkenecarboxylates are the preferred starting materials. Particularly important in industry are $C_1$-$C_4$-alkyl 4-pentenoates and $C_1$-$C_4$-alkyl 3-pentenoates and mixtures thereof. Suitable examples are ethyl 4-pentenoate, propyl 3-pentenoate, ethyl 2-pentenoate and mixtures thereof. Methyl 4-pentenoate and methyl 3-pentenoate are particularly preferred.

The $C_4$-$C_{20}$-alkenecarboxylic esters are reacted with carbon monoxide and hydrogen. As a rule, the hydrogen:carbon monoxide molar ratio in the gas mixture is from 1:10 to 100:1, in particular from 1:1 to 40:1.

The hydroformylation is carried out at from 30° to 150° C. in liquid phase. The reaction is advantageously carried out at from 50° to 120° C., usually under from 0.01 to 30 bar, advantageously from 1 to 30 bar. Pressures from 1 to 20 bar have proven particularly suitable.

The reaction is advantageously carried out in the presence of solvents. Examples of suitable solvents are aromatic hydrocarbons such as toluene or xylene, as well as the ω-formylalkanecarboxylic esters produced in the hydroformylation or the high boilers produced in the hydroformylation.

The hydroformylation is carried out in the presence of rhodium carbonyl complexes and at least one tertiary organic polyphosphite with from 2 to 6 phosphorus atoms. The concentration of the rhodium complex catalyst is generally from 10 to 1000 rpm, calculated as rhodium metal, preferably from 10 to 500 ppm rhodium and, in particular, from 25 to 350 ppm rhodium.

Generally from 2 to 100, preferably from 3 to 50, mol of polyphosphite are employed per gram atom of rhodium (which is the total of complexed and free polyphosphite). Fresh polyphosphite can be added to the reaction at any time in order to keep the concentration of free, uncomplexed phosphite constant. The rhodium carbonyl polyphosphite complex catalyst can be prepared separately before use. As a rule, however, the catalytically active components are formed in the reaction medium from a catalyst precursor, such as rhodium carbonyl acetylacetonate, rhodium oxide, rhodium carbonyl, rhodium nitrate or rhodium acetate and the polyphosphite ligand. The rhodium component preferably employed is rhodium carbonyl acetylacetonate or rhodium acetate and is reacted with the polyphosphite ligand in the presence of a solvent in order to from the precursor of the catalytically active complex which is introduced together with excess polyphosphite into the reaction in order to form in situ under the reaction conditions the active modified rhodium carbonyl complex.

Preferred tertiary organic phosphite have 2 to 4, in particular 2, phosphorus atoms. In each case one bond on each phosphorus atom is linked via an oxygen bridge to an arylene or bisarylene which is at least divalent, eg. di- to tetravalent, and has up to 12 carbons, to an alkylene which has from 2 to 8 carbons and can contain an oxygen in the chain, or to a radical with up to 16 carbons and to isolated aryl radicals, eg.

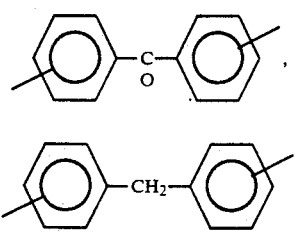

The two remaining bonds on each phosphorus atom are each linked via an oxygen bridge to a divalent arylene or bisarylene with up to 20 carbons, to an alkylene with from 4 to 8 carbons, or to a radical with two isolated aryl radicals, as defined above, via the aryl radicals. The aryl and bisaryl radicals preferably have $C_1$–$C_4$-alkoxy groups, especially methoxy groups, furthermore $C_1$–$C_4$-alkyl groups, especially t-butyl groups, as substituents in the o and p position.

Preferred polyphosphites are compounds of the formula I

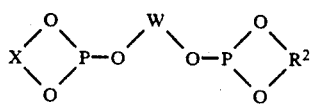

where

X is a divalent bisarylene or R1,

W is a divalent substituted or unsubstituted arylene, bisarylene or alkylene and $R^1$ and $R^2$ are identical or different and are a substituted or unsubstituted alkylene or ortho-arylene.

Preferred compounds of the formula I are those where X and W are bisarylene radicals, especially the radical of the formula II

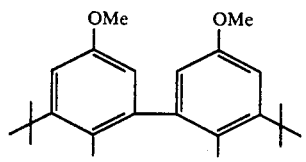

and $R^2$ is ortho-phenylene, 2,2-dimethyl-1,3-propylene or 1,1,2,2-tetramethylethylene. Also to be emphasized are compounds of the formula I where W, $R^1$ and $R^2$ are each, independently of one another, ortho-phenylene, 2,2-dimethyl-1,3-propylene or 1,1,2,2-tetramethylethylene.

The polyphosphites of the formula I can be prepared by conventional methods in a suitably selected sequence of phosphorus halide/alcohol condensation reactions.

a) for example, phosphorus trichloride is reacted with a diol to form a monochlorophosphite;

b) this intermediate is reacted with another diol to form the corresponding hydroxyl-substituted tertiary phosphite;

c) this tertiary phosphite intermediate is reacted with phosphorus trichloride to form the corresponding phosphorus dichloride intermediate;

d) and finally this dichloride is reacted with an appropriate diol to form the required bisphosphite.

Whereas this synthetic route is necessary for preparing non-symmetrically substituted phosphites, it is possible to prepare symmetrically substituted compounds by reacting the product from step a) with an appropriate diol in the molar ratio 2:1.

Said condensation reactions are usually carried out in a suitable solvent, eg. toluene in the presence of a base, such as triethylamine, as HCl acceptor.

Examples of suitable compounds of the formula I are

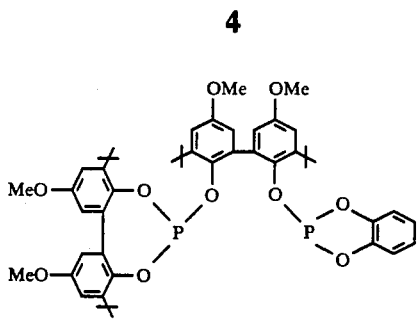

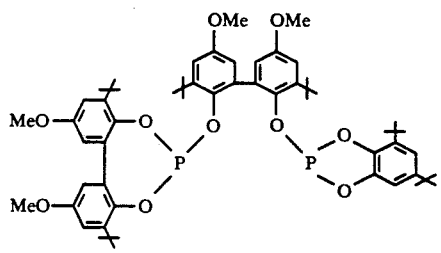

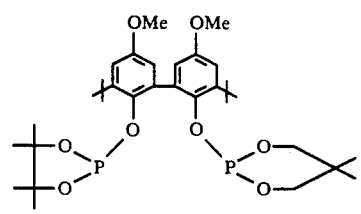

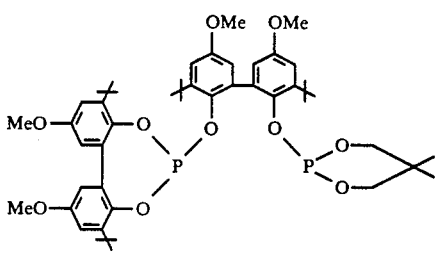

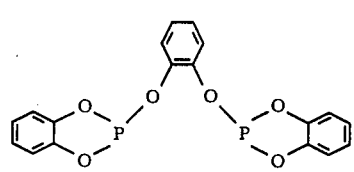

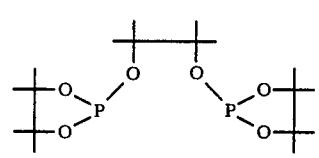

Another class of suitable polyphosphites are those of the formula III

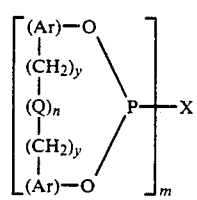

where

Ar are arylene radicals which have from 6 to 18 carbons and can be identical or different and may be substituted or unsubstituted;

X is an m-valent radical with from 2 to 30 carbons, selected form the group comprising alkylene, alkyleneoxyalkylene, arylene or arylene—(CH$_2$)$_y$—(Q)$_n$—(CH$_2$)$_y$—arylene where the arylene radicals are as defined above and Y is 0 or 1;

Q is divalent linker selected from oxygen, sulfur, —CO—, —CR$^1$R$^2$—, where R$^1$ and R$^2$ are each hydrogen or alkyl with 1 to 12 carbon atoms or phenyl, tolyl or anisyl, and —NR$^3$—, where R$^3$ is hydrogen or methyl;

n is 0 or 1, and m is an integer from 2 to 6.

In preferred compounds of the formula III, Ar is in each case o-phenylene, y and n are 0 and m is 2, and the two phenylene radicals can have alkyl groups with from 1 to 4 carbons or C$_1$-C$_4$-alkoxy groups, in particular methoxy and t-butyl groups, as substituents in the o and p position to the linkage to the oxygen bridge to the phosphorus atom.

A phosphite of the formula IV is particularly important in industry.

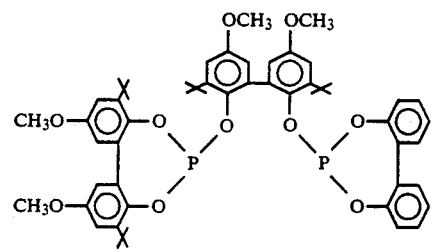

IV

Examples of other suitable compounds are those of the formulae V to XXIX.

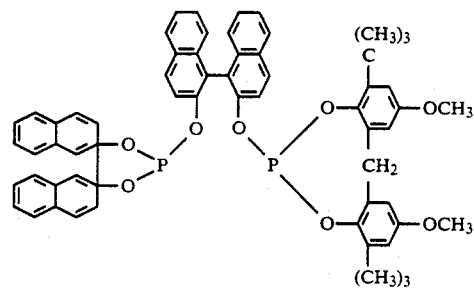

V

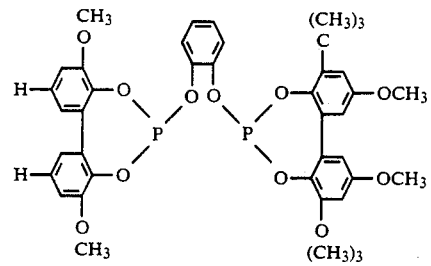

VI

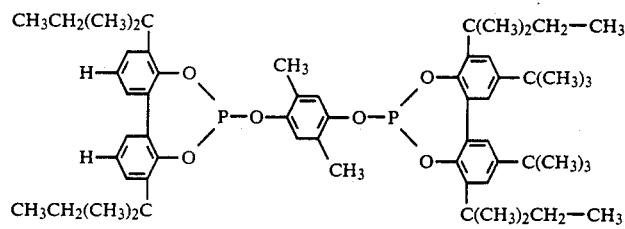

VII

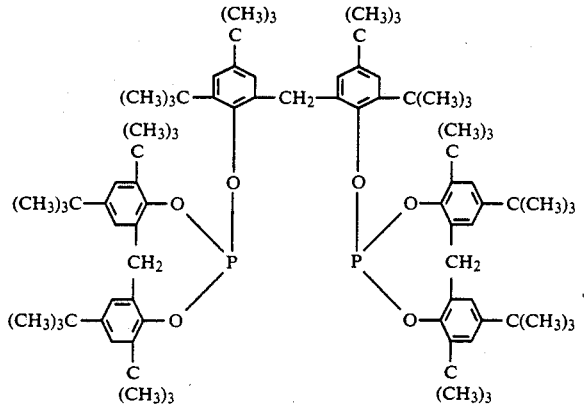

VIII

-continued
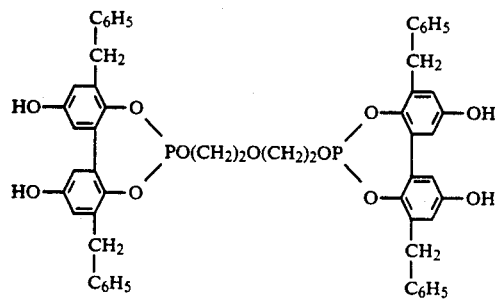
IX
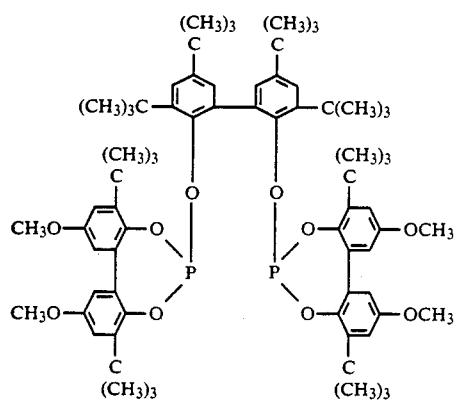
X
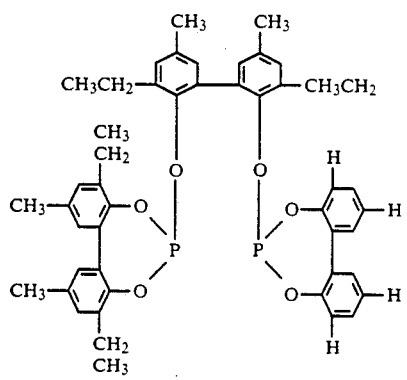
XI
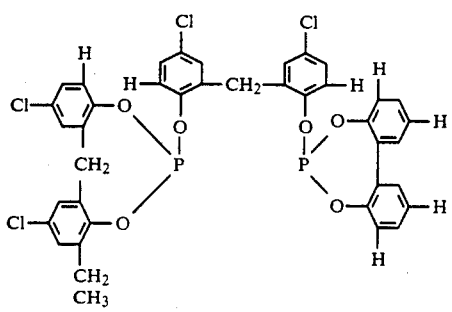
XII

-continued
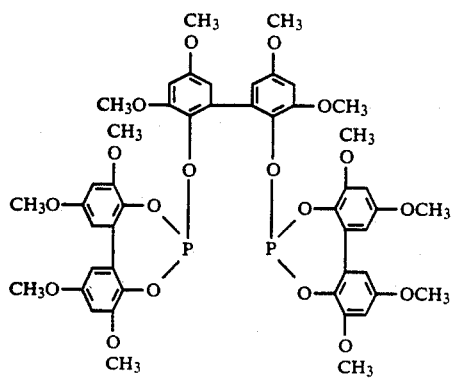
XIII
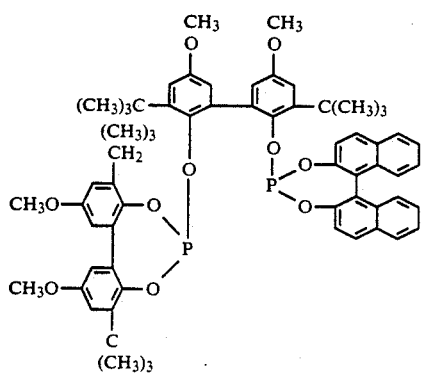
XIV
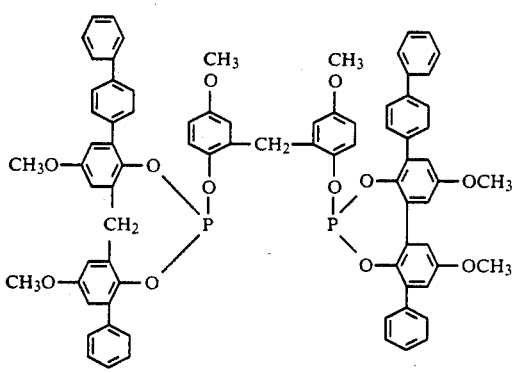
XV
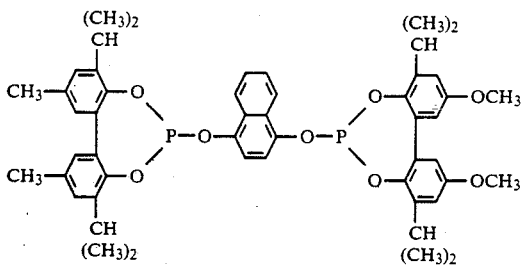
XVI
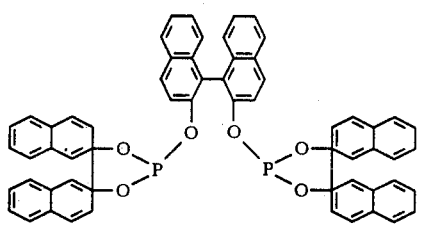
XVII -continued
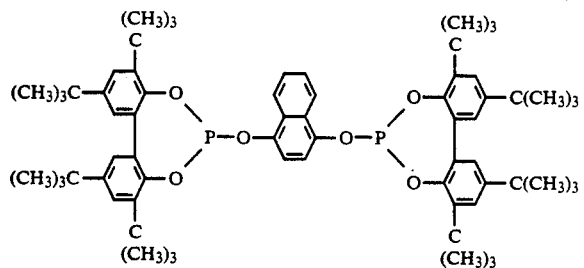   XVIII
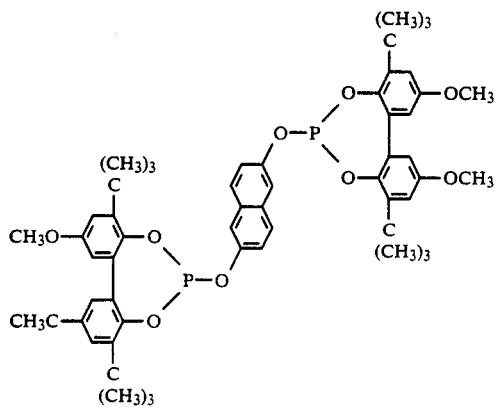   IXX
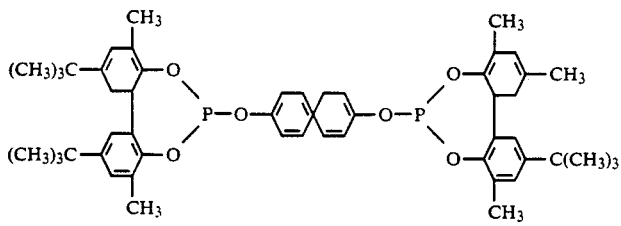   XX
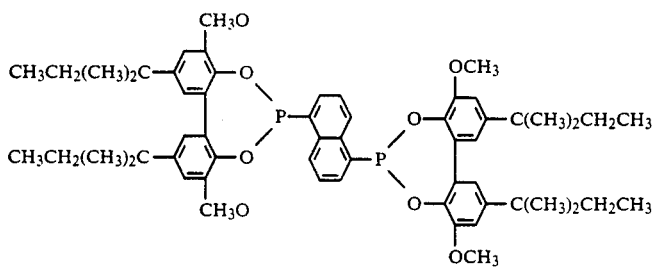   XXI
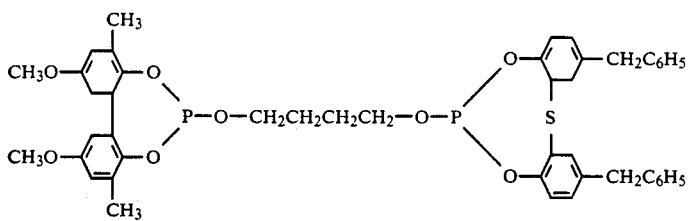   XXII
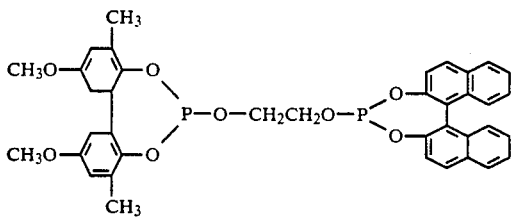   XXIII -continued
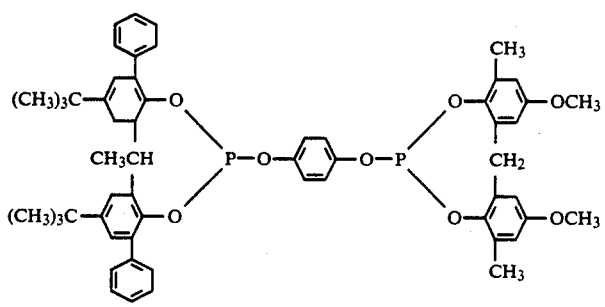
XXIV
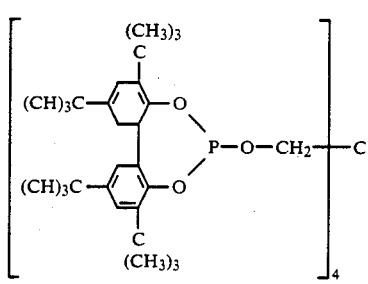
XXV
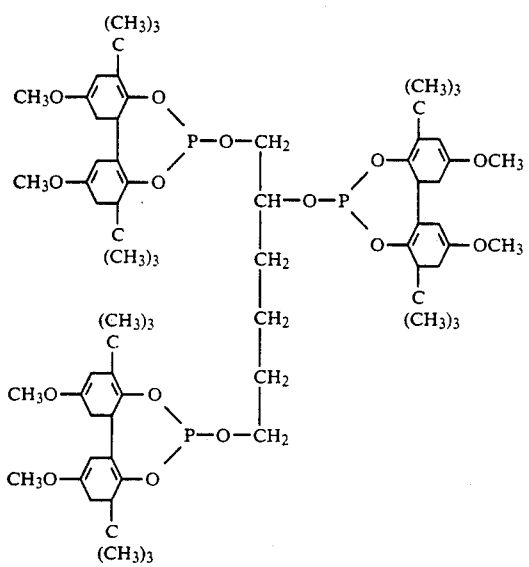
XXVI
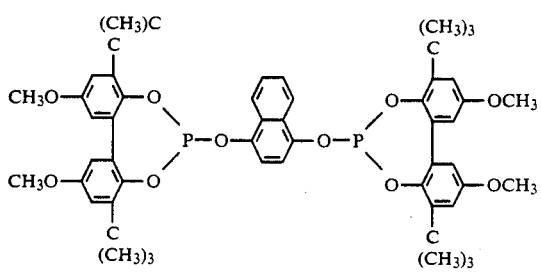
XXVII

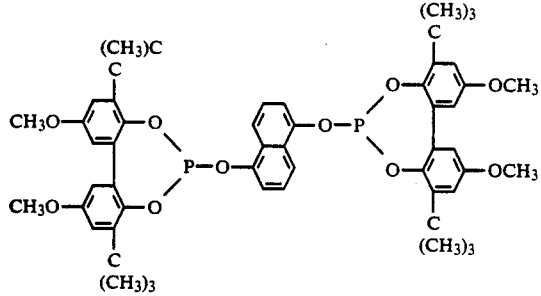

XXVIII

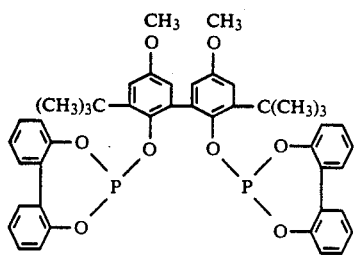

XXIX

Particularly preferred compounds of the formula III are those where
Ar are each phenylene which can have methoxy and/or $C_1$-$C_4$-alkyl as substituents,
Y is 0,
n is 0 and
m is 2.

Another class of preferred polyphosphites are those of the formula XXX

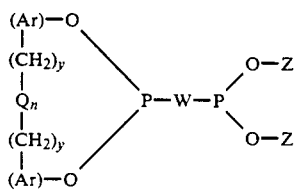 XXX where
Ar are arylene radicals which have from 6 to 18 carbons and can be identical or different and may be substituted or unsubstituted;
Y is 0 or 1;

Q is a divalent linker selected from oxygen, sulfur, —CO—, —$CR^1R^2$—, where $R^1$ and $R^2$ are each hydrogen or alkyl with 1 to 12 carbon atoms or phenyl, tolyl or anisyl, and —$NR^3$—, where $R^3$ is hydrogen or methyl;
n is 0 or 1;
W is a divalent substituted or unsubstituted arylene, bisarylene or alkylene, and Z are each alkyl, aryl, bisaryl, aralkyl or cycloalkyl radicals which can be identical or different.

In preferred compounds of the formula XXX, Ar is in each case o-phenylene, y and n are 0 and m is 2, and the two phenylene radicals can have alkyl groups with from 1 to 10 carbons or $C_1$-$C_4$-alkoxy groups, in particular methoxy and t-butyl groups, as substituents in the o and p position to the linkage to the oxygen bridge to the phosphorus atom.

W has the abovementioned meaning and the Z radicals can be identical or different and are each alkyl with from 1 to 18, in particularly 1 to 10, carbons, aryl, bisaryl or aralkyl with from 6 to 18 or cycloalkyl with from 5 to 8 carbons in the ring.

Examples of suitable compounds are those of the formulae

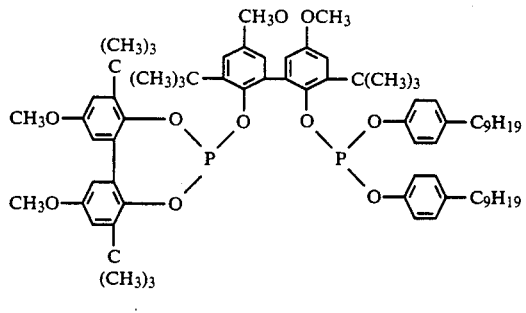 XXXI

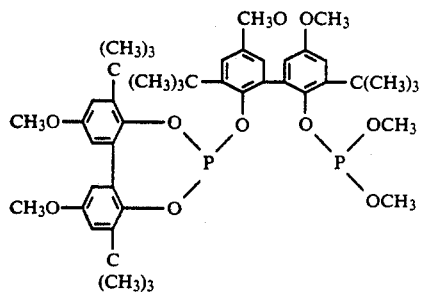

XXXII

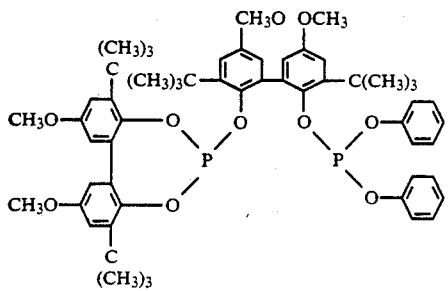

XXXIII

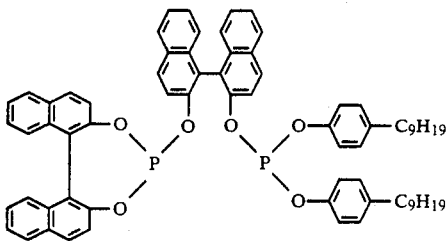

XXXIV

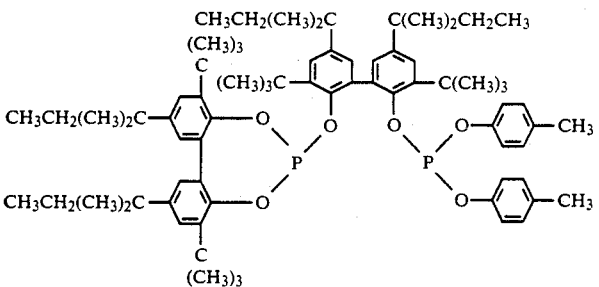

XXXV

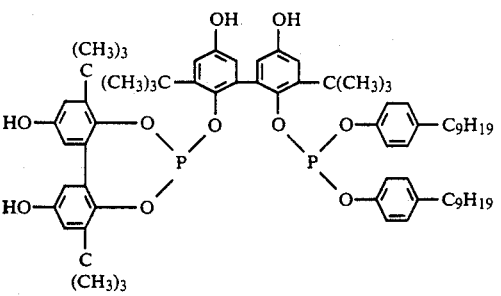

XXXVI

Compound of the formula XXXI are particularly preferred.

The ω-formylalkanecarboxylic esters which are produced can be removed from the reaction mixture by conventional methods, eg. distillation.

The ω-formylalkanecarboxylic esters which can be obtained by the process of the invention are suitable for preparing ω-amino carboxylic acids which are starting materials for polymers.

The process according to the invention is illustrated by the following examples.

EXAMPLE 1

100 g of methyl 3-pentenoate in 300 g of toluene as solvent are subjected to hydroformylation in a 1 l stirred autoclave. The reaction mixture contains as catalyst 2.23 g of the compound IV (2.33 mmol) and 40 mg (0.388 mmol) of rhodium in the form of the complex Rh(CO)₂acac (acac=acetylacetonate). The reaction mixture is heated to 100° C. and then adjusted to a pressure of 5 bar with a mixture of 50% by volume CO and 50% by volume H₂. The pressure in the reactor is kept at 5 bar during the reaction by injecting a gas mixture of the same composition through a pressure controller. After 5 hours, analysis of the reaction mixture shows the following conversion of methyl 3-pentenoate (in mol %):

| Conversion: | 95.5 mol % |
|---|---|
| Selectivity | |
| Methyl 4-pentenoate | 0.2 mol % |
| Methyl 2-cis-pentenoate | 0.2 mol % |
| Methyl 2-trans-pentenoate | 4.2 mol % |
| Methyl valerate | 4.8 mol % |
| Methyl 5-formylvalerate | 76.7 mol % |
| Methyl 4-formylvalerate | 7.8 mol % |
| Methyl 3-formylvalerate | 6.1 mol % |

The yield of the required product methyl 5-formylvalerate is 73.2% and the ratio of methyl 5-formylvalerate to methyl 3- and 4-formylvalerates is 85:15.

The selectivity for methyl 5-formylvalerate is 76.7% which is distinctly better than the prior art 68.7% (hydroformylation with cobalt). The improvement is even more evident on comparison of the yields (73.2% versus 22.3%) and of the ratios of methyl 5-formylvalerate to methyl 3- and 4-formylvalerates (85:15 versus 69:31). In addition, this result is achieved at distinctly lower pressure.

Direct hydroformylation of methyl 3-pentenoate to methyl 5-formylvalerate with conventional rhodium triphenylphosphine catalysts has very poor selectivity, as is evident from Comparative Example 1.

mixture of the same composition through a pressure controller. After 5 hours, analysis of the reaction mixture shows the following conversion of methyl 3-pentenoate (in mol %):

| Conversion: | 34.0 mol % |
|---|---|
| Selectivity | |
| Methyl 4-pentenoate | 0.6 mol % |
| Methyl 2-cis-pentenoate | 0.0 mol % |
| Methyl 2-trans-pentenoate | 1.1 mol % |
| Methyl valerate | 7.3 mol % |
| Methyl 5-formylvalerate | 8.8 mol % |
| Methyl 4-formylvalerate | 28.0 mol % |
| Methyl 3-formylvalerate | 54.2 mol % |

The yield of the required product methyl 5-formylvalerate is only 3.0% and the ratio of methyl 5-formylvalerate to methyl 3- and 4-formylvalerates is 10:90. Economic preparation of methyl 5-formylvalerate is therefore impossible by the process of Comparative Example 1.

The range of applications of the process according to the invention is illustrated hereinafter by means of some examples. These examples should not, however, by any means be regarded as restrictive because good results can also be expected outside the range described.

The influence of pressure and temperature is evident from Examples 2–9.

Example 1 was repeated but with 1.49 g of the compound IV (1.55 mmol) and with the pressures and temperatures specified in Table 1. The experiment under atmospheric pressure was carried out in a stirred (gas-introduction stirrer with hollow shaft) glass flask, with a mixture of 50% by volume CO and 50% by volume H₂ being passed in at a rate such that the exit gas produced about 1 bubble/second in a bubble counter.

TABLE 1

| Ex. No. | Pressure[a] bar | Temp. °C. | Conversion % | Selectivity, mol % | | | | | | 5-FVE FVE |
|---|---|---|---|---|---|---|---|---|---|---|
| | | | | 4-PE | 2-PE | VE | 5-FVE | 4-FVE | 3-FVE | |
| 2 | 4 | 90 | 61.9 | 2.2 | 12.5 | 2.8 | 66.6 | 9.1 | 6.8 | 81 |
| 3 | 4 | 100 | 84.7 | 0.7 | 13.1 | 6.4 | 68.4 | 7.4 | 4.1 | 86 |
| 4 | 4 | 110 | 60.9 | 5.1 | 38.8 | 4.9 | 43.8 | 4.9 | 2.6 | 85 |
| 5 | 0 | 90 | 63.1 | 3.8 | 22.1 | 9.5 | 55.6 | 7.3 | 1.7 | 86 |
| 6 | 0 | 100 | 67.5 | 3.9 | 52.3 | 16.3 | 22.6 | 4.2 | 0.8 | 82 |
| 7 | 6 | 100 | 91.2 | 0.0 | 15.4 | 5.9 | 59.5 | 11.9 | 7.4 | 76 |
| 8 | 8 | 100 | 81.7 | 0.6 | 20.3 | 4.8 | 54.9 | 11.4 | 7.9 | 74 |
| 9 | 10 | 110 | 94.7 | 0.0 | 14.6 | 9.3 | 55.8 | 12.7 | 7.6 | 73 |

[a]Summary
FVE: Formylvaleric ester
PE: Pentenoic ester

COMPARATIVE EXAMPLE 1

100 g of methyl 3-pentenoate in 300 g of toluene as solvent are subjected to hydroformylation in a 1 l stirred autoclave. The reaction mixture contains as catalyst 26.2 g of triphenylphosphine (100 mmol) and 40 mg (0.388 mmol) of rhodium in the form of the complex Rh(CO)₂acac (acac=acetylacetonate). The reaction mixture is heated to 100° C. and then adjusted to a pressure of 5 bar with a mixture of 50% by volume CO and 50% by volume H₂. The pressure in the reactor is kept at 5 bar during the reaction by injecting a gas It is evident that the hydroformylation succeeds even under atmospheric pressure but better yields are obtained in the range 4–6 bar (superatomspheric). The ratio of methyl 5-formylvalerate to methyl 3- and 4-formylvalerates decreases as the pressure is increased further.

The influence of the ligand/rhodium ratio is evident from Example 3 in Table 1 and Examples 10–12.

Example 1 was repeated but with the molar ratios of compound IV to Rh(CO)₂acac (0.388 mmol) specified in Table 2.

TABLE 2

| Example No. | IV/Rh | Conversion °C. % | | Selectivity, mol % | | | | | | 5-FVE FVE |
|---|---|---|---|---|---|---|---|---|---|---|
| | | | | 4-PE | 2-PE | VE | 5-FVE | 4-FVE | 3-FVE | |
| 3 (from Tab. 1) | 4 | | 84.7 | 0.7 | 13.1 | 6.4 | 68.4 | 7.4 | 4.1 | 86 |
| 10 | 8 | | 79.5 | 1.3 | 7.7 | 3.6 | 73.4 | 7.9 | 6.1 | 84 |
| 11 | 12 | | 78.8 | 1.0 | 7.0 | 3.3 | 74.9 | 7.8 | 6.1 | 84 |

TABLE 2-continued

| Example No. | IV/Rh | Conversion °C. % | Selectivity, mol % | | | | | | 5-FVE FVE |
|---|---|---|---|---|---|---|---|---|---|
| | | | 4-PE | 2-PE | VE | 5-FVE | 4-FVE | 3-FVE | |
| 12 | 20 | 81.8 | 1.5 | 6.1 | 3.5 | 74.8 | 7.9 | 6.1 | 84 |

4 bar superatmospheric pressure, in the other experiments 5 bar

It is evident that there is only a slight increase in the selectivity for methyl 5-formylvalerate by increasing the ligand/rhodium ratio from 4:1 to 20:1.

The influence of the solvent is evident from Examples 1 and 13 plus 14 (Table 3).

Example 1 was repeated but the solvents specified in Table 3 were used.

TABLE 3

| Ex. No. | Solvent | Conversion % | Selectivity, mol % | | | | | | 5-FVE FVE |
|---|---|---|---|---|---|---|---|---|---|
| | | | 4-PE | 2-PE | VE | 5-FVE | 4-FVE | 3-FVE | |
| 13 | — | 73.1 | 1.8 | 18.1 | 5.7 | 52.7 | 14.7 | 7.1 | 71 |
| 1 | Toluene | 95.5 | 0.2 | 4.4 | 4.8 | 76.7 | 7.8 | 6.1 | 85 |
| 14 | Palatinol-AH | 79.0 | 1.3 | 14.4 | 9.5 | 61.4 | 9.5 | 4.0 | 82 |

It is evident that it is in principle possible to omit a solvent but a better selectivity for methyl 5-formylvalerate is obtained in toluene. High-boiling solvents such as bis(2-ethylhexyl) phthalate are also suitable.

EXAMPLE 15

It is also possible to use mixtures of isomeric methyl pentenoates in the reaction, as shown by Example 15:

Example 1 was repeated but the following mixture was used in place of pure methyl 3-pentenoate:

| Methyl 4-pentenoate | 392 mmol | 44.8 mol % |
| Methyl 3-pentenoate | 329 mmol | 37.6 mol % |
| Methyl 2-pentenoate | 44 mmol | 5.0 mol % |
| Methyl valerate | 110 mmol | 12.6 mol % |

The composition of the reaction product was as follows:

| Methyl 4-pentenoate | 1 mol % |
| Methyl 3-pentenoate | 45 mol % |
| Methyl 2-pentenoate | 84 mol % |
| Methyl valerate | 158 mol % |
| Methyl 5-formylvalerate | 512 mol % |
| Methyl 4-formylvalerate | 50 mol % |
| Methyl 3-formylvalerate | 22 mol % |

Based on pentenoic ester mixture employed, this corresponds to a total conversion of 89.5%. The calculated selectivities are as follows:

| Methyl 2-pentenoate | 7.8 mol % |
| Methyl valerate | 6.9 mol % |
| Methyl 5-formylvalerate | 74.8 mol % |
| Methyl 4-formylvalerate | 7.3 mol % |
| Methyl 3-formylvalerate | 3.2 mol % |

The ratio of methyl 5-formylvalerate to methyl 3- and 4-formylvalerates is 88:12.

EXAMPLE 16

It is also possible to use methyl 2-pentenoate in the reaction, as shown by Example 16:

Example 1 was repeated but with methyl 2-trans-pentenoate in place of methyl 3-pentenoate. The results were as follows:

| Conversion: | 22.1 mol % |
| Selectivity | |
| Methyl 4-pentenoate | 0.4 mol % |
| Methyl 3-pentenoate | 13.6 mol % |
| Methyl 2-cis-pentenoate | 11.6 mol % |
| Methyl valerate | 62.8 mol % |
| Methyl 5-formylvalerate | 7.2 mol % |
| Methyl 4-formylvalerate | 1.0 mol % |
| Methyl 3-formylvalerate | 1.3 mol % |
| Methyl 2-formylvalerate | 1.9 mol % |

It is evident that the conversion of methyl 2-trans-pentenoate is only low and the predominant product is methyl valerate produced by hydrogenation. However, methyl 5-formylvalerate comprises 62% of the formylvalerates. With a conventional rhodium/triphenylphosphine catalyst the product is almost exclusively methyl 2-formylvalerate in high yield (pressure of 280 bar).

EXAMPLE 17

100 g of methyl 4-pentenoate in 300 g of toluene as solvent and 1.486 g of polyphosphite of the formula IV (1.5 mmol) and 40 mg (0.388 mmol) of rhodium in the form of the complex $Rh(CO)_2$ acetylacetonate are introduced into a 1 l stirred autoclave. The active catalyst is formed under the reaction conditions. The mixture is heated to 70° C. and then adjusted to a pressure of 4 bar with a mixture of 50% by volume carbon monoxide and 50% by volume hydrogen. When the pressure in the reactor falls below 2 bar during the reaction, the pressure is returned to 4 bar by injecting the same gas mixture. After 1.5 h, the reaction mixture is cooled, the pressure is released and the mixture is analyzed.

| Conversion of methyl 4-pentenoate: | 90.5 mol % |
| Selectivity | |
| Methyl valerate | 0.4 mol % |
| Methyl 5-formylvalerate | 92.9 mol % |
| Methyl 4-formylvalerate | 5.9 mol % |
| other byproducts | 0.8 mol % |

The ratio of methyl 5-formylvalerate to methyl 4-formylvalerate is 94:6.

EXAMPLE 18

100 g of methyl 3-pentenoate in 300 g of toluene as solvent are subjected to hydroformylation in 1 l stirred autoclave. The reaction mixture contains as catalyst 4.71 g of the compound XXXI (2.33 mmol) and 40 mg (0.388 mmol) of rhodium in the form of the complex Rh(CO)$_2$acac (acac=acetylacetonate). The reaction mixture is heated to 100° C. and then adjusted to a pressure of 5 bar with a mixture of 50% by volume CO and 50% by volume H$_2$. The pressure in the reactor is kept at 5 bar during the reaction by injecting a gas mixture of the same composition through a pressure controller. After 5 hours, analysis of the reaction mixture shows the following conversion of methyl 3-pentenoate (in mol %):

| Conversion: | 72.1 mol % |
|---|---|
| Selectivity | |
| Methyl 4-pentenoate | 0.7 mol % |
| Methyl 2-cis-pentenoate | 0.2 mol % |
| Methyl 2-trans-pentenoate | 9.2 mol % |
| Methyl valerate | 6.3 mol % |
| Methyl 5-formylvalerate | 71.9 mol % |
| Methyl 4-formylvalerate | 7.7 mol % |
| Methyl 3-formylvalerate | 4.0 mol % |

The yield of the required product methyl 5-formylvalerate is 51.8% and the ratio of methyl 5-formylvalerate to methyl 3- and 4-formylvalerates is 86:14.

EXAMPLE 19

100 g of methyl 3-pentenoate in 300 g of toluene as solvent are subjected to hydroformylation in 1 l stirred autoclave. The reaction mixture contains as catalyst 1.49 of the compound IV (1.684 mmol) and 40 mg (0.388 mmol) of rhodium in the form of the complex Rh(CO)$_2$acac (acac=acetylacetonate). The reaction mixture is heated to 100° C. and then adjusted to a pressure of 4 bar with a mixture of 505 by volume CO and 50% by volume H$_2$. The pressure in the reactor is kept at 4 bar during the reaction by injecting a gas mixture of the same composition through a pressure controller. After 5 hours, analysis of the reaction mixture shows the following conversion of methyl 3-pentenoate (in mol %):

| Conversion: | 49.3 mol % |
|---|---|
| Selectivity | |
| Methyl 4-pentenoate | 6.8 mol % |
| Methyl 2-cis-pentenoate | 2.1 mol % |
| Methyl 2-trans-pentenoate | 47.7 mol % |
| Methyl valerate | 2.6 mol % |
| Methyl 5-formylvalerate | 26.2 mol % |
| Methyl 4-formylvalerate | 9.5 mol % |
| Methyl 3-formylvalerate | 5.2 mol % |

The yield of the required product methyl 5-formylvalerate is 12.9% and the ratio of methyl 5-formylvalerate to methyl 3- and 4-methylvalerates is 64:36.

COMPARATIVE EXAMPLE 2

100 g of methyl 3-pentenoate in 300 g of toluene as solvent are subjected to hydroformylation in a 1 l stirred autoclave. The reaction mixture contains as catalyst 6.10 g of triphenyl phosphite (19.3 mmol) and 40 mg (0.388 mmol) of rhodium in the form of the complex Rh(CO)$_2$acac (acac=acetylacetonate). The reaction mixture is heated to 100° C. and then adjusted to a pressure of 4 bar with a mixture of 50% by volume CO and 50% by volume H$_2$. The pressure in the reactor is kept at 4 bar during the reaction by injecting a gas mixture of the same composition through a pressure controller. After 5 hours, analysis of the reaction mixture shows the following conversion of methyl 3-pentenoate (in mol %):

| Conversion: | 86.9 mol % |
|---|---|
| Selectivity | |
| Methyl 4-pentenoate | 0.4 mol % |
| Methyl 2-cis-pentenoate | 0.3 mol % |
| Methyl 2-trans-pentenoate | 7.9 mol % |
| Methyl valerate | 8.4 mol % |
| Methyl 5-formylvalerate | 27.4 mol % |
| Methyl 4-formylvalerate | 27.5 mol % |
| Methyl 3-formylvalerate | 28.1 mol % |

The yield of the required product methyl 5-formylvalerate is 23.8% and the ratio of methyl 5-formylvalerate to methyl 3- and 4-formylvalerate is 33:67.

It is evident that although the yield of formylvalerates in Comparative Example 2 is high, the required methyl 5-formylvalerate is produced to only a minor extent.

We claim:

1. A process for preparing ω-formyl-C$_4$-C$_{20}$-alkanecarboxylic esters by reacting C$_4$-C$_{20}$-alkenecarboxylic esters with carbon monoxide and hydrogen at from 30° to 150° C. in liquid phase in the presence of rhodium carbonyl complexes and in the presence of tertiary organic phosphites, which comprises using at least one tertiary organic polyphosphite which has from 2 to 6 phosphorus atoms in the molecule and in which, in each case, one bond on each phosphorus atom is linked via an oxygen bridge to a substituted or unsubstituted arylene or bisarylene which is at least divalent, to an alkylene which can contain an oxygen in the chain, or to a radical with two isolated aryl radicals via the aryl radicals, and two bonds on each phosphorus atom are linked via an oxygen bridge to a substituted or unsubstituted divalent arylene or bisarylene, to an alkylene or to a radical with two isolated aryl radicals via the aryl radicals, or two bonds on at least one phosphorus atom are, in each case, separately linked via an oxygen bridge in each case to a monovalent substituted or unsubstituted aryl, bisaryl, alkyl, aralkyl or cycloalkyl.

2. A process as claimed in claim 1, wherein the molar ratio of polyphosphite, calculated as phosphorus equivalent, to rhodium is from 1:1 to 300:1.

3. A process as claimed in claim 1, wherein a solvent inert under the reaction conditions is also used.

4. A process as claimed in claim 1, wherein the ω-formylalkanecarboxylic ester which is the final product in each case is used as solvent.

5. A process as claimed in claim 1, wherein the high boilers resulting from the hydroformylation are used as solvent.

6. A process as claimed in claim 1, wherein 3-pentenoic esters are used.

7. A process as claimed in claim 1, wherein 4-pentenoic esters are used.

8. A process as claimed in claim 1, wherein mixtures of 2-, 3-pentenoic esters are used.

9. A process as claimed in claim 1, wherein a polyphosphite of the formula IV

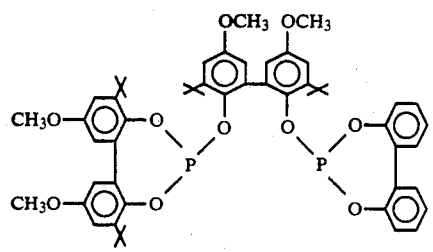
is used.
10. A process as claimed in claim 1, wherein a polyphosphite of the formula XXXI
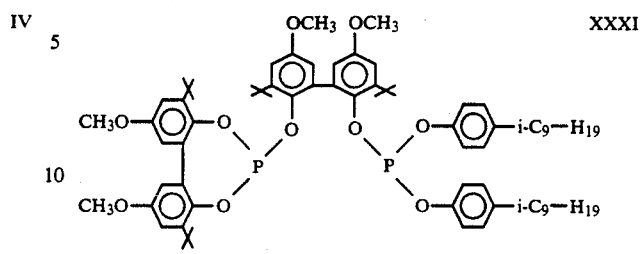
is used.
* * * * *

UNITED STATES PATENT AND TRADEMARK OFFICE
CERTIFICATE OF CORRECTION

PATENT NO. : 5,264,616
DATED : Nov. 23, 1993
INVENTOR(S) : ROEPER et al.

It is certified that error appears in the above-identified patent and that said Letters Patent is hereby corrected as shown below:

IN THE CLAIMS

Claim 8, column 24, line 66, after "3-" insert -- , and 4- --.

Signed and Sealed this

Twenty-fourth Day of May, 1994

Attest:

BRUCE LEHMAN

Attesting Officer      Commissioner of Patents and Trademarks